United States Patent [19]

Sangokoya

[11] Patent Number: 5,731,253
[45] Date of Patent: Mar. 24, 1998

[54] HYDROCARBYLSILLOXY - ALUMINOXANE COMPOSITIONS

[75] Inventor: Samuel A. Sangokoya, Baton Rouge, La.

[73] Assignee: Albemarle Corporation, Richmond, Va.

[21] Appl. No.: 508,005

[22] Filed: Jul. 27, 1995

[51] Int. Cl.⁶ .................. C07F 7/02; C07F 5/06; B01J 31/00; B01J 37/00

[52] U.S. Cl. .................. 502/102; 556/178; 556/179; 556/173; 502/103; 502/117; 502/114; 502/232; 502/235; 526/127; 526/943

[58] Field of Search .................. 502/102, 114, 502/235, 232; 556/173, 178, 179

[56] References Cited

U.S. PATENT DOCUMENTS

| | | | |
|---|---|---|---|
| 3,002,986 | 10/1961 | Hyde | 556/173 |
| 3,184,418 | 5/1965 | Woods et al. | 556/173 |
| 3,413,242 | 11/1968 | Roberts et al. | 556/173 |
| 3,657,159 | 4/1972 | Vandenberg | 260/2 |
| 3,661,878 | 5/1972 | Aishima et al. | 260/88.2 F |
| 3,740,384 | 6/1973 | Ballard et al. | 260/94.9 |
| 3,787,323 | 1/1974 | Aishima et al. | 502/118 |
| 3,969,332 | 7/1976 | Gloriod et al. | 526/128 |
| 4,036,867 | 7/1977 | Piekarski et al. | 260/448 A |
| 4,472,519 | 9/1984 | McDaniel | 502/103 |
| 4,931,517 | 6/1990 | Fujita | 526/128 |
| 4,945,076 | 7/1990 | Piotrowski et al. | 502/117 |
| 5,017,714 | 5/1991 | Welborn, Jr. | 556/12 |
| 5,026,798 | 6/1991 | Canich | 526/127 |
| 5,034,549 | 7/1991 | Piotrowski et al. | 556/10 |
| 5,057,475 | 10/1991 | Canich et al. | 502/104 |
| 5,061,668 | 10/1991 | Hoxmeier et al. | 502/117 |
| 5,122,491 | 6/1992 | Sangokoya | 502/103 |
| 5,614,654 | 3/1997 | Miyake et al. | 556/173 |

FOREIGN PATENT DOCUMENTS

| | | | |
|---|---|---|---|
| 2112965 | 8/1994 | Canada | |
| 0 133 750 | 3/1985 | European Pat. Off. | 556/173 |
| 0 271 716 | 6/1988 | European Pat. Off. | 556/173 |
| 0129368 | 7/1989 | European Pat. Off. | |
| 0367503 | 5/1990 | European Pat. Off. | |
| 0418937 | 3/1991 | European Pat. Off. | |
| 0561476 | 9/1993 | European Pat. Off. | |
| 0621279 | 10/1994 | European Pat. Off. | |
| 46-3966 | 1/1971 | Japan | 556/173 |

OTHER PUBLICATIONS

H. Schmidbaur et al., J.Am.Chem.Soc., vol. 84, pp. 1069–1070, Mar. 19, 1963.

Chem. Abstracts, vol. 39, #6426e, 1963.

C. Jeffrey Brinker et al., "Sol–Gel Science: The Physics and Chemistry of Sol–Gel Processing", New York, Academic Press, pp. 2–19, 52–59, 66–71, 98–103, 108–115, 138–139, 160–163, 218–223, 228–233, 1990.

Siloxy–substituted Aluminoxanes: Synthesis from Polydialkylsiloxanes and Trimethylaluminum, and Application as Aluminosilicate Precursors, J. Mater. Chem. 1993, 3(6), 597–602, Landry, et al.

Ceram. Trans., 19 (Adv. Composite Matter.) 35–41 (1991), "Design and Synthesis of Polymeric Precursors to Aluminosilicates", by Allen W. Apblett, et al. (no month available).

*Primary Examiner*—Glenn Caldarola
*Assistant Examiner*—J. Pasterczyk
*Attorney, Agent, or Firm*—Philip M. Pippenger

[57] ABSTRACT

Siloxy-aluminoxane compositions which are the reaction products of hydrocarbylsiloxanes substantially-free of Si—OH groups, and aluminoxanes and which have improved solubility and stability in solution even at up to 60 weight percent when compared to the original aluminoxane. The compositions in combination with metallocenes of transition lanithanide and actinide metals form catalysts which can be used in the polymerization of olefins such as ethylene.

51 Claims, No Drawings

HYDROCARBYLSILLOXY - ALUMINOXANE COMPOSITIONS

This process relates generally to soluble aluminoxane derivatives and more particularly to siloxy-aluminoxane compositions obtained by the reaction of hydrocarbylsiloxanes and aluminoxanes which, in the presence of metallocenes, form catalytically active compositions for olefin polymerization.

U.S. Pat. No. 3,740,384 discloses that the addition of dihydroxysiloxane to non-metallocene organo-zirconium catalyst systems in the absence of aluminoxanes gave improved catalyst activity in olefin polymerization. Likewise, U.S. Pat. No. 4,945,076 describes the improved activity in olefin polymerization which is obtained by the addition of dihydroxysiloxane to a catalyst system consisting of a metallocene and an aluminoxane. The resulting ethylene polymer is said to have acquired a lower melt flow rate (MFR) than those produced without the silicon compound. U.S. Pat. No. 5,034,549 discloses that a preformed catalyst component is obtained by the reaction of dihydroxysiloxane or silicon diol with a zirconocene. The patent further alleges that this catalyst component, when used in conjunction with methyl-aluminoxane, formed a good catalyst system for olefin polymerization.

All the above mentioned disclosures describe the use of alkoxy-silanes having Si—O—C bonds, silicon diols having Si—OH bonds and dihydroxysiloxanes having both the Si—O—Si and Si—OH bonds. The reagents used in the present invention, namely hydrocarbylsiloxanes, have the Si—O—Si bonds but not the Si—OH bonds. The chemical reactivity of the hydrocarbyl-siloxanes is significantly different from those of the silanols, silyl ethers, silyl esters and hydroxy disiloxanes (1. *Comprehensive Organometallic Chemistry*, Vol. 2, Chap. 9; Pergamon Press, 1982: 2. *Comprehensive Organic Chemistry*, Vol. 3, Chap. 13 Pergamon Press N.Y. 1979). Those skilled in the art would appreciate the fact that silicon compounds having Si—OH bonds generally undergo dehydration and condensation reactions. These reactions are rarely observed in the case of hydrocarbylsiloxanes. Thus, one could not anticipate any obvious similarity between the reactions of silanols, silyl ethers and silyl esters compared to hydrocarbylsiloxanes. In fact one would not expect to isolate under similar conditions, the same product described in U.S. Pat. No. 5,034,549 by substituting a hydrocarbylsiloxane for the dihydroxysiloxane or silicon diol, as this would require the breaking of Si—O bond which is more difficult than breaking the SiO—H bond.

Methylaluminoxane is the most important aluminoxane used as a co-catalyst in polymerization reactions. It is usually obtained in aromatic solvents, in which it is only temporarily soluble. Methylaluminoxane solutions are usually plagued with instability with respect to gel formation or solid precipitation within a short period. Dilute toluene solutions of methylaluminoxane (10 weight percent or less) are reasonably stable to gel formation or solid precipitation for a couple of weeks at room temperature. However, the stability of methylaluminoxane solution drastically decreases as the concentration increases to about 20 weight percent or more.

My U.S. Pat. No. 5,391,529, whose disclosure is incorporated herein by reference, relates to aluminoxanes reacted with alkyldisiloxanes to form novel, soluble siloxy-aluminum compounds which, in combination with metallocenes, provide olefin polymerization catalysts having very high activity.

It has now been found that the reaction products of aluminoxanes with other hydrocarbylsiloxanes, such as aryl, alkyl-aryl and cycloalkyl disiloxanes and polysiloxanes, including cyclic polysiloxanes, provide aluminoxanes containing hydrocarbylsiloxane moieties which impart stability to the aluminoxanes such that the aluminoxanes are not only more soluble in organic solvents but do not easily form gels during storage. For example, a concentrated methylaluminoxane (MAO) solution (20 weight percent or above) can be treated with cyclic or linear siloxane compounds to give solution stable, concentrated siloxy-methylaluminoxane compositions, which, after further solvent removal, produce 25–60 weight percent siloxy-methylaluminoxane solutions having enhanced solution stability. Alternatively, one can treat a dilute solution of the MAO solution with siloxanes to form stable siloxy-methylaluminoxane compositions which can optionally be further concentrated to give 25–60 weight percent siloxy-methylaluminoxane solutions.

In accordance with this invention there is provided a siloxy-aluminoxane composition which comprises an aluminoxane which contains hydrocarbylsiloxane moieties which are substantially free of Si—OH bonds, wherein the molar portion of aluminum to hydrocarbylsiloxane is from about 1:1 to 1000:1.

Also provided is an olefin polymerization catalyst comprising a metallocene of a transition, lanthanide or actinide metal and a siloxy-aluminoxane composition which comprises an aluminoxane which contains hydrocarbylsiloxane moieties which are substantially free of Si—OH bonds, wherein the molar portion of aluminum to hydrocarbylsiloxane is from about 1:1 to 1000:1.

The siloxy-aluminoxane compositions are obtainable by the reaction of an aluminoxane and a hydrocarbyldi- or polysiloxane such that the aluminoxane contains hydrocarbylsiloxane moieties which are chemically bonded thereto.

Preferred aluminoxanes for use in making the siloxy-aluminoxane compounds are hydrocarbylaluminoxanes.

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 4 to 20 of the repeating units:

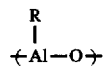

where R is $C_1$–$C_{10}$ alkyl and especially preferred are methylaluminoxanes (MAO). The methylaluminoxanes can contain some higher alkyl groups to improve their solubility. Such modified methylaluminoxanes are described, for example, in U.S. Pat. No. 5,157,008.

The aluminoxanes can be prepared as known in the art by the partial hydrolysis of trialkylaluminum compounds. The trialkylaluminum compounds can be hydrolyzed by adding either free water or water containing solids, which can be either hydrates or porous materials which have absorbed water. Because it is difficult to control the reaction by adding water per se, even with vigorous agitation of the mixture, the free water is preferably added in the form of a solution or a dispersion in an organic solvent. Suitable hydrates include salt hydrates such as, for example, $CuSO_4 \bullet 5H_2O$, $Al_2(SO_4)_3 \bullet 18H_2O$, $FeSO_4 \bullet 7H_2O$, $AlCl_3 \bullet 6H_2O$, $Al(NO_3)_3 \bullet 9H_2O$, $MgSO_4 \bullet 7H_2O$, $ZnSO_4 \bullet 7H_2O$, $Na_2SO_4 \bullet 10H_2O$, $MgCl_2 \bullet 6H_2O$, $Na_3PO_4 \bullet 12H_2O$, $LiBr \bullet 2H_2O$, $LiCl \bullet 1H_2O$, $LiI \bullet 2H_2O$, $LiI \bullet 3H_2O$, $KF \bullet 2H_2O$, $NaBr \bullet 2H_2O$ and the like and alkali or alkaline earth metal hydroxides such as, for example, NaOH●H$_2$O, NaOH●2H$_2$O, Ba(OH)$_2$●8H$_2$O, KOH●2H$_2$O, CsOH●1H$_2$O, LiOH●1H$_2$O and the like. Mixtures of any of the above hydrates can be used. The mole ratios of free water or water in the hydrate to total alkyl aluminum compounds in the mixture can vary widely, such as for example from about 2:1 to 1:4 with ratios of from about 4:3 to 1:3.5 being preferred.

Such processes for preparing hydrocarbylaluminoxanes are described, for example, in U.S. Pat. No. 4,908,463. The methylaluminoxanes contain varying amounts, of from about 5 to 35 mole percent, of the aluminum value as unreacted trimethylaluminum.

The hydrocarbylsiloxanes for use in the invention have hydrocarbyl groups which preferably contain from about 1 to 30 carbon atoms and include linear and/or branched alkyl groups which contain from about 1 to 24 carbon atoms, cycloalkyl groups which contain from about 3 to 24 carbon atoms and alkylaryl or aryl groups which contain from about 6 to 30 carbon atoms. The hydrocarbylsiloxanes are chosen from disiloxanes and linear or cyclic polysiloxanes. The hydrocarbylsiloxanes contain the Si—O—Si bond and are substantially free of Si—OH bonds. The hydrocarbylsiloxanes can contain mixed hydrocarbyl groups. Non-limiting examples of hydrocarbylsiloxanes include hexamethyldisiloxane, hexaethyldisiloxane, tetramethyldisiloxane, tetramethyldicyclohexyldisiloxane, tetramethyldibutyldisiloxane, hexaphenyldisiloxane, diphenyltetramethyldisiloxane, tetraphenyldimethyldisiloxane, hexamethylcyclotrisiloxane, octamethylcyclotetrasiloxane, octaphenylcyclotetrasiloxane, octamethyltrisiloxane, and the like.

The siloxy-aluminoxane compositions can be prepared by reacting the aluminoxane and hydrocarbylsiloxane in an organic solvent medium in molar portions of aluminum in the aluminoxane to hydrocarbyldisiloxane of from about 1:1 to 1000:1 and preferably from about 1:1 to 50:1. Mixtures of aluminoxanes and/or hydrocarbylsiloxanes can be used in forming the compositions. Any inert organic solvent can be used as the reaction medium. Non-limiting examples of solvents include aliphatic hydrocarbons such as pentane, isopentane, hexane, cyclohexane, heptane, octane, decane, dodecane, hexadecane, octadecane and the like with those having carbon numbers of 5 to 10 being preferred and aromatic hydrocarbons such as benzene, toluene, xylene, cumene and the like with those having carbon numbers of 6 to 20 being preferred. Generally amounts of solvent to provide a total concentration of reactants of from about 3 to 30 wt. percent are used.

Reaction temperatures usually range from about 0° to 200° C. Preferred reaction temperatures range from about 25° to 150° C.

The siloxy-aluminoxane compounds can be used in combination with metallocenes to provide olefin polymerization catalysts. Such metallocenes are well known in the art and non-limiting examples include the metallocenes described in U.S. Pat. Nos. 4,892,851, 5,017,714, 5,026,798, 5,145,819, 5,296,434, 5,324,800 and 5,329,033, whose teachings with respect to such metallocenes are incorporated herein by reference. Illustrative examples of such metallocenes are bis-(cyclopentadienyl)-zirconium dimethyl, bis-(cyclopentadienyl)-zirconium dichloride, bis-(cyclopentadienyl)-monomethyl-monochloride, bis-(cyclopentadienyl)-titanium dichloride, bis-(cyclopentadienyl)-titanium difluoride, cyclopentadienyl-zirconium tri-(2-ethyl-hexanoate), bis-cyclopentadienyl)-zirconium hydrogen chloride, bis-(cyclopentadienyl) hafnium dichloride and the like.

The catalyst components are used in proportions to provide mole ratios of transition metal atom to aluminum atom of from about 0.0002:1 to 0.2:1 and preferably 0.0005:1 to 0.02:1. The catalyst components can be used in solution or deposited on a solid support. The solid support can be any particulate solid, and particularly porous supports such as talc or inorganic oxides, or resinous support material such as polyolefins. Preferably, the support material is an inorganic oxide in finely divided form.

Suitable inorganic oxide support materials which are desirably employed include Group IIA, IIIA, IVA or IVB metal oxides such as silica, alumina, silica-alumina and mixtures thereof. Other inorganic oxides that may be employed either alone or in combination with the silica, alumina or silica-alumina are magnesia, titania, zirconia, and the like. Other suitable support materials are finely divided polyolefins such as finely divided polyethylene.

The catalysts are effective to produce olefin polymers and especially ethylene polymers and ethylene/α-olefin copolymers. Examples of olefins that can be polymerized in the presence of the catalysts of the invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Polymerization of ethylene or copolymerization with ethylene and an α-olefin having 3 to 10 carbon atoms is preferable. Such polymerizations may be performed in either the gas or liquid phase (e.g. in a solvent, such as toluene, or in a diluent, such as heptane). The polymerization can be conducted at conventional temperatures (e.g., 0° to 120° C.) and pressures (e.g., ambient to 50 kg/cm$^2$) using conventional procedures as to molecular weight regulations and the like.

The invention is further illustrated by, but is not intended to be limited to, the following examples.

The following examples were carried out under inert atmosphere conditions, using Schlenk glassware and a vacuum line, in conjunction with a N$_2$-drybox. Solvents were distilled using standard methods. Filtration and vacuum distillation were done inside a N$_2$-drybox and distillates were collected in a trap at −78° C. Siloxanes were purchased from commercial sources and used without further purification. Aluminoxanes were obtained from stock solutions produced by Albemarle Corporation.

Despite the enhanced solution stability of the siloxy-aluminoxane compositions, compared to regular aluminoxane solutions, the polymerization activity is not adversely affected. On the contrary, significant activity improvement is observed for certain siloxy-aluminoxane compositions.

EXAMPLE 1

Solid methylaluminoxanes (MAO, 38 mmol Al) was suspended in hexane (50 mL). The mixture was stirred at room temperature (30 minutes). Hexamethyldisiloxane (HMDS, 4.7 mmol) was then slowly added via syringe. After stirring for 16 hours, the mixture was filtered. The hexane solution was then concentrated to dryness by vacuum distillation. The resulting solid siloxy-MAO product contained 65% of the initial aluminum value. Silicon-29 and proton NMR showed one sharp singlet each for the siloxy group. Additionally, $^1$H NMR showed the usual broad peak for methylaluminoxane in the aluminum alkyl region. The sharp signals suggest a probable end capping environment of the siloxy group in the MAO structure.

EXAMPLE 2

Solid MAO (122 mmol Al) was suspended in hexane (300 mL) in a reaction flask. HMDS (60 mmol) was added via syringe. The mixture was stirred for about 30 minutes at room temperature and then heated to 70° C. (oil bath) for another 12 hours. The slurry was filtered and the filtrate was concentrated to give a white solid material which contained 67% of the initial aluminum value. $^{29}$Si and $^1$H NMR data are similar to those obtained for Example 1.

EXAMPLE 3

Solid MAO (60 mmol Al) was placed in hexane (100 mL). To the slurry was added HMDS (75 mmol). The mixture was magnetically stirred for about 20 hours and then filtered. The filtrate was concentrated to give white granular siloxy-MAO derivative.

The preceding Examples 1–3 showed that the variation of HMDS concentration, reaction time and thermal conditions did not significantly alter either the product yield or the spectroscopic data of the resulting solid siloxy-MAO derivative.

EXAMPLE 4

This preparation was done to investigate the effect of a mixed solvent system, toluene/hexane. A toluene solution of MAO (350 mmol Al) was placed in a reaction flask and hexane (150 g) was added. The HMDS (90 mmol) was then slowly added via syringe. The mixture was stirred for about 14 hours at room temperature. After filtration, the clear liquid which contained 90% of the original aluminum value, was concentrated to give a white solid siloxy-MAO product.

$^1$H NMR data showed more sharp peaks overlapping the usual MAO broad peak in the aluminum alkyl region, than was seen in the alkane product.

EXAMPLE 5

Solid MAO (30 mmol Al) was dissolved in toluene (20 mL) and then HMDS (5 mmol) was added. The reaction was carried out as described in Example 1. The resulting solid product contained 92% of the original aluminum value. $^1$H NMR contained several singlet peaks buried under the usual broad MAO peak.

EXAMPLE 6

Solid MAO (75 mmol Al) was added to a toluene solvent (50 mL). To this solution was then added HMDS (30 mmol) from a syringe. The mixture was stirred at room temperature for about 4 hours. Then hexane (50 mL) was added and the mixture was stirred for another 2 hours and filtered. The filtrate was concentrated to dryness to give a solid product which contained 85% of the initial aluminum value.

The $^1$H NMR of the solid, hexane derived siloxy-MAO product showed only one sharp singlet peak in the aluminum alkyls region regardless of the concentration of HMDS. By contrast, similar spectra for the solid MAO, toluene derived products, showed several sharp singlet peaks in the aluminum alkyls region. Furthermore, as the molar ratio of HMDS increased the number of singlet peaks attributable to the siloxy derivatives increased. The reason for this unequivocal solvent effect is not known.

EXAMPLE 7

Solid MAO (75 mmol Al) was dissolved in toluene (50 mL). To this solution was added HMDS (75 mmol). The mixture was stirred at room temperature for about 20 hours. Hexane (50 mL) was added and then the mixture was stirred for another 4 hours. After filtration and concentration, the resulting solid siloxy-MAO compound contained 88% of the original aluminum value.

$^1$H NMR of the solid compound showed several singlet peaks (Me$_3$SiO) buried under the broad MAO peaks.

The starting material in the above described reactions was solid MAO. This was obtained by removal of toluene from the MAO solution via vacuum distillation. For commercial purposes, it is desirable to avoid extra processing requirements. The following examples describe the formation of siloxy-MAO compositions directly from the initial toluene solution of MAO.

EXAMPLE 8

An MAO solution in toluene (271 mmol Al, 78 g of a 9.4% Al by weight solution) was placed in a reaction flask. HMDS (68 mmol) was slowly added at room temperature. The mixture was stirred for about 12 hours and then heat (oil bath, 80° C.) was applied for about 2 hours. The mixture was filtered and the filtrate was found to contain 92% of the original aluminum value.

This siloxy-MAO solution was found to be more active, compared to the original MAO solution, in an ethylene polymerization test (Table 1).

EXAMPLE 9

To a solution of MAO in toluene (300 mmol Al) was added HMDS (150 mmol). The reaction was carried out as described in Example 8. The filtrate contained 93% of the original aluminum value. The resulting siloxy-MAO solution was found to be very active in ethylene polymerization (Table 1).

EXAMPLE 10

An MAO solution in toluene (272 mmol Al) was placed in a reaction flask. HMDS (204 mmol) was slowly added from a syringe. The reaction was carried out as described in Example 8. The resulting filtrate contained about 82% of the original aluminum value. A significant reduction in the trimethylaluminum (TMA) content (from 30% TMA to 13% TMA) was observed for this product.

The product in conjunction with zirconocene dichloride is highly active in ethylene polymerization (Table 1).

EXAMPLE 11

A solution of MAO in toluene (272 mmol Al) was treated with HMDS (272 mmol). The reaction was carried out as described in Example 8. About 86% of the original aluminum value was recovered after filtration. The liquid product was found to be very active in ethylene polymerization (Table 1).

EXAMPLE 12

MAO solution (194 mmol Al) was allowed to react with hexaethyldisiloxane (HEDS, 38.8 mmol). The reaction was carried out as described in Example 8. The resulting filtrate contained 79% of the original aluminum value.

A portion of the filtrate was concentrated under vacuum to give an oily product.

EXAMPLE 13

A solution of isobutylaluminoxane (IBAO, 109 mmol Al) in cyclohexane was treated with HMDS (27 mmol). The mixture was stirred at room temperature for about 2 hours and then heated (oil bath) at 100° C. for another 10 hours. The clear solution was concentrated under vacuum to give a thick oily product. Ordinarily, a solid product would have resulted after similar treatment of the original IBAO solution. $^1$H NMR showed broad peaks from 0.2 to 0.4 ppm which is attributable to the siloxy-aluminoxane group. All the other IBAO peaks are still present.

EXAMPLE 14

An MAO solution in toluene (871 g, 1446 mmol Al) was placed in a reaction bottle. Then, hexamethyldisiloxane (23.5 g, 144.6 mmol), 10%) was added slowly at room temperature. After addition, the mixture was stirred at room temperature for about two hours. Then, the mixture was heated at 80° C. (oil bath) for another two hours. On cooling to room temperature, the mixture was filtered through a medium frit to obtain a clear colorless solution product (884 g).

A portion of the liquid product (772 g) was concentrated at 50° C./0.1 mm Hg to give a product which contains 32 weight percent MAO product. This product exhibits remarkable solution stability such that after 16 months no sign of gel formation or solid precipitation was observed, even at this high concentration. Furthermore, a drastic reduction in the TMA content of the original MAO solution was also observed. Thus, TMA content was reduced from the original 20 mole percent to 14 mole percent of the total aluminum content, which is about 30% reduction. This result is in sharp contrast to popular belief that excess TMA is required to improve MAO solubility and stability.

Some of the product was also concentrated to dryness under reduced pressure to obtain a free flowing solid product.

$^1$H NMR of both the solid and liquid products showed Si—Me peaks and also revealed additional fine structures in the Al—Me region which are not observable in the corresponding spectra for regular untreated MAO.

EXAMPLE 15

A concentrated solution of MAO in toluene (232 g, 1114 mmol Al) was placed in a reaction bottle. Hexamethyldisiloxane (18 g, 111.4 mmol) was added and the mixture stirred at room temperature for 6 hours. Then the mixture was filtered through a coarse frit and then through a medium frit to give clear colorless liquid product.

The siloxy-methylaluminoxane product contains 27 weight percent MAO product. The product was stored in a dry glass bottle inside a 2N-drybox. This product started to show the first sign of gel formation after 5 weeks. Regular MAO solution of similar concentration usually takes less than 2 weeks to show gel formation. This product is drastically less stable compared to the product in Example 14. This, therefore, shows the importance of heating and removal of excess HMDS and gaseous byproducts as done in example 1.

EXAMPLE 16

A dilute solution of MAO in toluene (140 g, 232 mmol Al) was placed in a reaction bottle. Octamethylcyclotetrasiloxane (6.9 g, 23.2 mmol, 10%) was added slowly. The mixture was stirred at room temperature for 2 hours. A slight gas evolution with foaming was observed. Then, the mixture was heated at 90°–100° C. (oil bath) for about 4 hours. After filtration through a medium frit, a clear colorless liquid product resulted.

A part of the product was concentrated under reduced pressure to give 25 weight percent MAO product solution, which did not show any visible sign of gel formation over a six month period.

EXAMPLE 17

A concentrated solution of MAO in toluene (60 g, 264 mmol Al) was placed in a reaction bottle. Octamethylcyclotetrasiloxane (1.5 g, 5 mmol, 2%) was added, followed by heating at 80° C. (oil bath) for 2 hours. On cooling, the mixture was filtered through a medium frit. The product was further concentrated to remove some volatiles. The resulting solution contains 25 weight percent product.

EXAMPLE 18

To a solution of MAO in toluene (800 g, 1360 mmol Al) was added octaphenylcyclotetrasiloxane (2.2 g, 2.72 mmol, 0.2%). The reaction was carried out as described in Example 17. Lots of foaming was observed during and after filtration. The product was further concentrated to give 35 weight percent MAO product solution.

EXAMPLE 19

MAO solution (93 g, 418 mmol Al) was allowed to react with hexamethylcyclotrisiloxane (1.9 g, 8.4 mmol, 2%) as described in Example 17. A foamy but clear and colorless liquid product was obtained after filtration. The product was further concentrated to give 36 weight percent MAO product solution.

EXAMPLE 20

A solution of MAO in toluene (86 g, 361 mmol Al) was treated with tetraphenyldimethyldisiloxane (1.5 g, 3.6 mmol, 1%) and the reaction carried out as described in Example 17. The product was further concentrated under reduced pressure to give 31 weight percent solution.

EXAMPLE 21

MAO solution (85 g, 357 mmol Al) was treated with tetraphenyldimethyldisiloxane (0.15 g, 0.36 mmol, 0.1%) as described in Example 17. The experiment was designed to determine the minimum amount of siloxane required to provide enhance solution stability for concentrated MAO solution.

The product was further concentrated to obtain 36 weight percent solution.

EXAMPLE 22

To a solution of MAO in toluene (91 g, 410 mmol Al) was added diphenyltetramethyldisiloxane (5.9 g, 20.5 mmol, 5%). The reaction was carried out as described in Example 17. After filtration, the product was further concentrated to give 45 weight percent solution.

POLYMERIZATION

Ethylene polymerization was conducted in a Parr reactor (600 mL) equipped with a cooling coil, magnetic stirrer, pressure gauge and a gas inlet. The catalyst system, siloxy-MAO and zirconocene dichloride, are dissolved in toluene (300 mL). The loading was done in a dry-box after which the reactor was assembled in a well vented hood. Ethylene was passed into the reactor at 60 psi for 10 minutes while the temperature was maintained at about 90° C.

After cooling down to room temperature, the reactor contents were poured into a beaker where an equal volume of methanol was added to destroy the catalyst system. The polyethylene was collected by filtration and then dried in a vacuum oven.

EXAMPLES 23 and 24

Solid samples obtained from Examples 1 and 5 were separately employed in conjunction with zirconocene dichloride to conduct ethylene polymerization tests as described above. Results are shown in Table 1.

EXAMPLES 25 to 28

Toluene samples of the siloxy-aluminoxanes obtained respectively from Examples 8 to 11 were separately employed in the presence of zirconocene dichloride to conduct ethylene polymerization as described above. Results are shown in Table 1.

EXAMPLES 29 to 31

Siloxy-aluminoxane compositions obtained from Examples 16, 17 and 18 were separately used in the presence of zirconocene dichloride to polymerize ethylene as described above.

Results indicate that alkyl and aryl cyclic polysiloxanes are also useful in forming soluble siloxy-methylaluminoxane compositions which are polymerization active.

COMPARISON

A comparative polymerization was carried out using regular methylaluminoxane (MAO) solution in toluene (9.4 wt. % Al) in conjunction with zirconocene dichloride without the addition of disiloxane. The results are shown in Table 1.

Table 1 shows that no significant additional activity was gained as the molar ratio of HMDS was increased. However, the data in this table show a notable increase (about 50%) in the activity of the siloxy-MAO derivatives as compared to the regular MAO under similar conditions.

What is claimed is:

1. A siloxy-aluminoxane composition comprising an aluminoxane which contains terminal hydrocarbylsiloxane moieties which are free of Si—OH groups, wherein the molar ratio of aluminum to hydrocarbylsiloxane is from about 1:1 to 1000:1, said siloxy-aluminoxane composition being free of Si—OH groups, and the aluminoxane of said siloxy-aluminoxane composition having been formed by partial hydrolysis of trialkylaluminum.

2. The composition of claim 1 wherein the hydrocarbyl groups in said hydrocarbylsiloxane moieties have from about 1 to 30 carbon atoms and said aluminoxane is an alkylaluminoxane wherein the alkyl groups contain from about 1 to 10 carbon atoms.

3. The composition of claim 1 wherein said hydrocarbylsiloxane moieties are derived from an aryldisiloxane or a linear or cyclic aryl polysiloxane.

4. The composition of claim 3 wherein said hydrocarbylsiloxane moieties are derived from a hydrocarbylsiloxane selected from the group consisting of octaphenylcyclotetrasiloxane, diphenyltetramethyldisiloxane, hexaphenyldisiloxane, and tetraphenyldimethyldisiloxane and said aluminoxane is methylaluminoxane.

5. The composition of claim 2 wherein said hydrocarbylsiloxane moieties are derived from a linear, branched or cyclic alkyl polysiloxane.

6. The composition of claim 2 wherein said hydrocarbylsiloxane moieties are derived from a hydrocarbylsiloxane selected from the group consisting of tetramethyldibutyldisiloxane, tetramethyldicyclohexyldisiloxane, hexamethyldisiloxane, hexamethylcyclotrisiloxane, and octamethylcyclotetrasiloxane, octamethyltrisiloxane and said alkylaluminoxane is methylaluminoxane.

7. An olefin polymerization catalyst comprising the substance formed by combining (i) a metallocene of a transition, lanthanide or actinide metal and (ii) a siloxy-aluminoxane composition which comprises an aluminoxane which contains terminal hydrocarbylsiloxane moieties which are free of Si—OH groups, wherein the molar ratio of aluminum to

TABLE 1

Siloxy-MAO Derivatives/Ethylene Polymerization[a]

| Example # | HMDS[d] (%) | Aluminum (Moles × $10^{-3}$) | Zirconocene Dichloride (Moles × $10^{-6}$) | Al/Zr Mole Ratio | Activity g(PE)/mol. Zr · atm · hr ($10^6$) | Activity Compared to Regular MAO | PE (g) |
|---|---|---|---|---|---|---|---|
| 23 | 15 | 16.7 | 12.4 | 1347 | 4.74 | NA[b] | 40 |
| 24 | 15 | 16.7 | 12.4 | 1347 | 4.98 | NA[b] | 42 |
| 25 | 25 | 10 | 6.8 | 1470 | 10.16 | 1.8 | 47 |
| 26 | 50 | 10 | 6.8 | 1470 | 9.74 | 1.7 | 45 |
| 27 | 75 | 10 | 6.8 | 1470 | 9.08 | 1.6 | 42 |
| 28 | 100 | 10 | 6.8 | 1470 | 9.08 | 1.6 | 42 |
| 29 | [e]OMCTS (10) | 10 | 6.8 | 1470 | 7.57 | 1.4 | 35 |
| 30 | OMCTS (2) | 10 | 6.8 | 1470 | 7.35 | 1.3 | 34 |
| 31 | [f]OPCTS (0.2) | 10 | 6.8 | 1470 | 12.54 | 2.2 | 58 |
| Comparison | Regular MAO | 10 | 6.8 | 1470 | 5.62 | 1[c] | 26 |

[a]Conducted at 60 psi ethylene, 90° C., in toluene (300 mL) for 10 minutes.
[b]NA → Not applicable, because the Al/Zr ratio is different.
[c]Control experiment using standard regular MAO solution in toluene.
[d]15% HMDS is defined as the product obtained from 100 mmol Al/15 mmol HMDS.
[e]OMCTS = octamethylcyclotetrasiloxane
[f]OPCTS = octaphenylcyclotetrasiloxane hydrocarbylsiloxane is from about 1:1 to 1000:1, said siloxy-aluminoxane composition being free of Si—OH groups, and the aluminoxane of said siloxy-aluminoxane composition having been formed by partial hydrolysis of trialkylaluminum.

8. The catalyst of claim 7 in which the mole ratio of transition, lanthanide, or actinide metal atoms of said metallocene to aluminum atoms of in said siloxy-aluminoxane composition is from about 0.0002:1 to 0.2:1.

9. The catalyst of claim 8 wherein said mole ratio is from about 0.0005:1 to 0.02:1.

10. The catalyst of claim 7 wherein the hydrocarbyl groups in said hydrocarbylsiloxane moieties have from about 1 to 30 carbon atoms and said aluminoxane is a hydrocarbylaluminoxane wherein the hydrocarbyl groups contain from about 1 to 10 carbon atoms.

11. The catalyst of claim 10 wherein said hydrocarbylsiloxane moieties are derived from an aryldisiloxane or a linear or cyclic aryl polysiloxane.

12. The catalyst of claim 11 wherein said hydrocarbylsiloxane moieties are derived from a hydrocarbylsiloxane selected from the group consisting of octaphenylcyclotetrasiloxane, diphenyltetramethyldisiloxane, hexaphenyldisiloxane, and tetraphenyldimethyldisiloxane and said hydrocarbylaluminoxane is methylaluminoxane.

13. The catalyst of claim 10 wherein said hydrocarbylsiloxane is a linear, branched or cyclic alkyl polysiloxane.

14. The catalyst of claim 10 wherein said hydrocarbylsiloxane moieties are derived from a hydrocarbylsiloxane selected from the group consisting of hexamethyldisiloxane, hexamethylcyclotrisiloxane, and octamethylcyclotetrasiloxane and said hydrocarbylaluminoxane is methylaluminoxane.

15. The catalyst of claim 10 in which the mole ratio of transition, lanthanide, or actinide metal atoms of said metallocene to aluminum atoms of said siloxy-aluminoxane composition is from about 0.0002:1 to 0.2:1.

16. The catalyst of claim 15 wherein said mole ratio is from about 0.0005:1 to 0.02:1.

17. A method of stabilizing an aluminoxane, formed by partial hydrolysis of trialkylaluminum and having a content of trimethylaluminum, against gel formation and reducing the trimethylaluminum content of said aluminoxane, said method comprising reacting said aluminoxane with a hydrocarbyldisiloxane which is free of Si—OH groups or a hydrocarbylpolysiloxane which is free of Si—OH groups.

18. An aluminoxane composition comprising a hydrocarbon solvent solution of a siloxy-aluminoxane composition which comprises an aluminoxane which contains terminal hydrocarbylsiloxane moieties and is free of Si—OH groups in a molar ratio of aluminum to hydrocarbylsiloxane of from about 1:1 to 1000:1, the aluminoxane of said siloxy-aluminoxane composition having been formed by partial hydrolysis of trialkylaluminum.

19. The composition of claim 18 wherein said aluminoxane is methylaluminoxane and said composition contains up to about 60 weight percent of said methylaluminoxane.

20. The composition of claim 19 wherein said composition contains from about 25 –60 weight percent of said methylaluminoxane and said composition shows increased storage stability compared to methylaluminoxane which does not contain said hydrocarbylsiloxane moieties.

21. A siloxy-aluminoxane composition comprising the product of reaction between (a) an aluminoxane formed by partial hydrolysis of trialkylaluminum and (b) a hydrocarbylsiloxane free of Si—OH groups in a molar ratio of aluminum to hydrocarbylsiloxane of from about 1:1 to about 1000:1, said hydrocarbylsiloxane being selected from the group consisting of (i) hydrocarbyldisiloxanes that have aryl, alkyl-aryl or cycloalkyl hydrocarbyl groups therein, and (ii) linear or cyclic hydrocarbylpolysiloxanes, said siloxy-aluminoxane composition being free of Si—OH groups.

22. The composition of claim 21 wherein each of the hydrocarbyl groups in said hydrocarbylsiloxane has 1 to 30 carbon atoms, and wherein said aluminoxane is an alkylaluminoxane wherein each of the alkyl groups contains 1 to 10 carbon atoms.

23. The composition of claim 21 wherein said molar ratio is from about 1:1 to 50:1.

24. The composition of claim 21 wherein said hydrocarbylsiloxane is a hydrocarbyldisiloxane that has aryl, alkyl-aryl or cycloalkyl hydrocarbyl groups therein.

25. The composition of claim 24 wherein said hydrocarbyldisiloxane is diphenyltetramethyldisiloxane, hexaphenyldisiloxane, tetraphenyldimethyldisiloxane, or tetramethyldicyclohexyldisiloxane.

26. The composition of claim 25 wherein the aluminoxane is methylaluminoxane.

27. The composition of claim 21 wherein said hydrocarbylsiloxane is a linear or cyclic hydrocarbylpolysiloxane.

28. The composition of claim 27 wherein said hydrocarbylpolysiloxane is hexamethylcyclotrisiloxane, octamethyltrisiloxane, octamethylcyclotetrasiloxane, or octaphenylcyclotetrasiloxane.

29. The composition of claim 28 wherein the aluminoxane is methylaluminoxane.

30. An olefin polymerization catalyst comprising the composition formed by combining (i) a metallocene of a transition, lanthanide, or actinide metal, and (ii) a siloxy-aluminoxane composition comprising the product of reaction between (a) an aluminoxane formed by partial hydrolysis of trialkylaluminum and (b) a hydrocarbylsiloxane free of Si—OH groups in a molar ratio of aluminum to hydrocarbylsiloxane of from about 1:1 to about 1000:1, said hydrocarbyisiloxane being selected from the group consisting of (i) hydrocarbyldisiloxanes that have aryl, alky-aryl or cycloalkyl hydrocarbyl groups therein, and (ii) linear or cyclic hydrocarbylpolysiloxanes, said siloxy-aluminoxane composition being free of Si—OH groups.

31. The catalyst of claim 30 wherein the mole ratio of metal atoms of said metallocene to aluminum atoms of said siloxy-aluminoxane composition is from about 0.0002:1 to 0.2:1.

32. The catalyst of claim 31 wherein said mole ratio is from about 0.0005:1 to 0.02:1.

33. The catalyst of claim 30 wherein each of the hydrocarbyl groups in said hydrocarbylsiloxane has 1 to 30 carbon atoms, and said aluminoxane is an alkylaluminoxane wherein each of the alkyl groups contains 1 to 10 carbon atoms.

34. The catalyst of claim 30 wherein said molar ratio is from about 1:1 to 50:1.

35. The catalyst of claim 34 wherein said hydrocarbylsiloxane is a hydrocarbyldisiloxane that has aryl, alky-aryl or cycloalkyl hydrocarbyl groups therein.

36. The catalyst of claim 35 wherein said hydrocarbyldisiloxane is diphenyltetramethyldisiloxane, hexaphenyldisiloxane, tetraphenyldimethyldisiloxane, or tetramethyldicyclohexyldisiloxane, and wherein the aluminoxane is methylaluminoxane.

37. The catalyst of claim 34 wherein said hydrocarbylsiloxane is a linear or cyclic hydrocarbylpolysiloxane.

38. The catalyst of claim 37 wherein said hydrocarbylpolysiloxane is hexamethylcyclotrisiloxane, octamethyltrisiloxane, octamethylcyclotetrasiloxane, or octaphenylcyclotetrasiloxane, and wherein the aluminoxane is methylaluminoxane.

39. The catalyst of claim 36 wherein the mole ratio of metal atoms of said metallocene to aluminum atoms of said siloxy-aluminoxane composition is from about 0.0002:1 to 0.2:1.

40. The catalyst of claim 39 wherein said mole ratio is from about 0.0005:1 to 0.02:1.

41. The catalyst of claim 30 wherein the metal of the metallocene is titanium, zirconium or hafnium.

42. A method of stabilizing an aluminoxane, formed by partial hydrolysis of trialkylaluminum and having a content of trimethylaluminum, against gel formation and reducing the trimethylaluminum content of said aluminoxane, said method comprising reacting said aluminoxane with a hydrocarbylsiloxane which is free of Si—OH groups.

43. The method of claim 42 wherein said reaction is conducted in an organic solvent medium at a reaction temperature in the range of about 0° to 200° C., and wherein the molar ratio of aluminoxane to hydrocarbylsiloxane is from about 1:1 to 1000:1.

44. The method of claim 42 wherein said reaction is conducted in a hydrocarbon solvent medium at a reaction temperature in the range of about 25° to 150° C., and wherein the molar ratio of aluminoxane to hydrocarbyisiloxane is from about 1:1 to 50:1.

45. An aluminoxane composition comprising a hydrocarbon solvent solution of (a) an aluminoxane and (b) the product of reaction between an aluminoxane and a hydrocarbyisiloxane free of Si—OH groups wherein the molar ratio of aluminum in said aluminoxane composition to hydrocarbylsiloxane is from about 1:1 to about 1000:1, said hydrocarbylsiloxane being selected from the group consisting of (i) hydrocarbyldisiloxanes that have aryl, alkyl-aryl or cycloalkyl hydrocarbyl groups therein, and (ii) linear or cyclic hydrocarbylpolysiloxanes, said siloxy-aluminoxane composition being free of Si—OH groups, said aluminoxanes of (a) and (b) having been formed by partial hydrolysis of trialkylaluminum.

46. The composition of claim 45 wherein said aluminoxane is methylaluminoxane, and wherein said solution is a 25 to 60 weight percent solution.

47. A process for producing a siloxy-aluminoxane composition having increased storage stability, said process comprising reacting in an organic solvent medium at a reaction temperature in the range of about 0° to about 200° C. (a) an aluminoxane formed by partial hydrolysis of trialkylaluminum and (b) a hydrocarbylsiloxane free of Si—OH groups selected from the group consisting of hydrocarbyldisiloxanes, linear hydrocarbylpolysiloxanes, and cyclic hydrocarbylpolysiloxanes, the molar ratio of aluminum in said aluminoxane to hydrocarbylsiloxane being from about 1:1 to about 1000:1, whereby the storage stability of said siloxy-aluminoxane composition is greater than the storage stability of the aluminoxane from which it was prepared.

48. A process according to claim 47 wherein the hydrocarbyl groups in said hydrocarbylsiloxane each have from about 1 to 30 carbon atoms and said aluminoxane is an alkylaluminoxane wherein the alkyl groups each contain from about 1 to 10 carbon atoms.

49. A process according to claim 47 wherein the hydrocarbyl groups of said hydrocarbylsiloxane are selected from the group consisting of (i) alkyl groups which contain from about 1 to 24 carbon atoms, (ii) cycloalkyl groups which contain from about 3 to 24 carbon atoms, and (iii) aryl or alkyl-aryl groups which contain from about 6 to 30 carbon atoms, and wherein said aluminoxane is methylaluminoxane.

50. A process according to claim 49 wherein said hydrocarbylsiloxane is a hydrocarbyldisiloxane that has aryl, alkyl-aryl or cycloalkyl hydrocarbyl groups therein, wherein said medium is an inert hydrocarbon medium and wherein said molar ratio is from about 1:1 to 50:1.

51. A process according to claim 49 wherein said hydrocarbylsiloxane is a hydrocarbylpolysiloxane, wherein said medium is an inert hydrocarbon medium and wherein said molar ratio is from about 1:1 to 50:1.

* * * * *

UNITED STATES PATENT AND TRADEMARK OFFICE
CERTIFICATE OF CORRECTION

PATENT NO. : 5,731,253
DATED : March 24, 1998
INVENTOR(S) : Samuel A. Sangokoya

It is certified that error appears in the above-indentified patent and that said Letters Patent is hereby corrected as shown below:

Column 11, line 6, reads "of in said" and should read -- of said --.

Signed and Sealed this

Eighteenth Day of May, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,731,253
DATED : March 24, 1998
INVENTOR(S) : Samuel A. Sangokoya

It is certified that error appears in the above-identified patent and that said Letters Patent is hereby corrected as shown below:

Title Page, Item [56], Reference omitted:
5,391,529   02/1995   Sangokoya   502/103

Title Page, Item [56], Reference 5,122,491 reads:
"Sangokoya   502/103"
And should read:
Kioka et al.   502/117--

Signed and Sealed this

Twenty-eighth Day of September, 1999

Attest:

Q. TODD DICKINSON

*Attesting Officer*     Acting Commissioner of Patents and Trademarks